United States Patent [19]

Provine

[11] Patent Number: 5,688,993
[45] Date of Patent: Nov. 18, 1997

[54] METHOD FOR MODIFYING CATALYST PERFORMANCE DURING THE GAS PHASE SYNTHESIS OF VINYL ACETATE

[75] Inventor: William Douglas Provine, Greenville, Del.

[73] Assignee: E. I. Du Pont de Nemours and Company, Wilmington, Del.

[21] Appl. No.: 604,594

[22] Filed: Feb. 21, 1996

Related U.S. Application Data

[63] Continuation-in-part of Ser. No. 577,451, Dec. 22, 1995, abandoned.

[51] Int. Cl.[6] .................................................. C07C 67/05
[52] U.S. Cl. ............................................................ 560/245
[58] Field of Search ................................................ 560/245

[56] References Cited

U.S. PATENT DOCUMENTS

| | | | |
|---|---|---|---|
| 3,479,392 | 11/1969 | Stern et al. | 260/497 |
| 3,634,497 | 1/1972 | Budke | 260/497 |
| 3,658,888 | 4/1972 | Hornig | 560/245 |
| 3,830,834 | 8/1974 | Kronig | 560/245 |
| 3,969,274 | 7/1976 | Frampton | 252/456 |
| 4,048,096 | 9/1977 | Bissot | 252/430 |
| 4,093,559 | 6/1978 | Fernholz et al. | 252/443 |
| 4,126,645 | 11/1978 | Collins | 260/677 |
| 4,128,595 | 12/1978 | Montgomery | 260/677 |
| 4,345,105 | 8/1982 | Rogers | 585/271 |
| 4,347,392 | 8/1982 | Cosyns et al. | 585/259 |
| 4,409,396 | 10/1983 | Dempf | 560/245 |
| 4,551,443 | 11/1985 | Hudson | 502/313 |
| 4,577,047 | 3/1986 | Hudson | 585/260 |
| 4,762,956 | 8/1988 | Liu et al. | 585/259 |
| 4,940,687 | 7/1990 | Liu et al. | 502/333 |
| 5,059,732 | 10/1991 | Cosyns et al. | 585/259 |
| 5,274,181 | 12/1993 | Bartley et al. | 560/245 |
| 5,292,931 | 3/1994 | Wirtz et al. | 560/245 |
| 5,347,046 | 9/1994 | White et al. | 560/245 |

FOREIGN PATENT DOCUMENTS

| | | |
|---|---|---|
| 0 685 451 A1 | 2/1995 | European Pat. Off. . |
| 1 282 641 | 5/1966 | Germany . |
| Sho 41-85840 | 12/1966 | Japan . |
| Sho 42-55161 | 8/1967 | Japan . |
| 666523 | 10/1966 | South Africa . |
| 1082845 | 9/1964 | United Kingdom . |
| 1188737 | 3/1968 | United Kingdom . |

OTHER PUBLICATIONS

International Search Report for International application No. PCT/US 96/20121, AD–6427–A, International filing date 18 Dec. 1996.

Copelin, Manufacture of Vinyl Acetate, *Ethylene and Its Industrial Derivatives*, 948–951, 1969.

Vinyl Acetate, *Hydrocarbon Processing*, 163–164, Apr. 1978.

Masuhiko Tamura and Teruo Yasui, Catalytic Action of Palladium in the Synthesis of Vinyl Acetate by the Ethylene Method, *Shokubai 21*, No. 1, 54–60, 1979 (Transtation only).

Yen–Chen Yen, Catalyst, *Vinyl Acetate*, Report No. 15A/Supplement A, 33–34, Jun. 1972.

Setsuo Yoshioka and Chikara Omae, Ethylene Process Vinyl Acetate Synthesis, *The Journal of The Petroleum Institute*, 15, #6, 459–466 (21–28), 1972.

*Primary Examiner*—Michael L. Shippen
*Attorney, Agent, or Firm*—Craig H. Evans

[57] ABSTRACT

An improved method for synthesizing vinyl acetate by the gas phase reaction of acetic acid with ethylene in the presence of oxygen. At least two catalyst modifiers are used, each causing a different level of catalyst activity. The relative mounts of the catalyst modifiers are used to fine tune the productivity of the catalyst.

21 Claims, 2 Drawing Sheets

METHOD FOR MODIFYING CATALYST PERFORMANCE DURING THE GAS PHASE SYNTHESIS OF VINYL ACETATE

CROSS REFERENCE TO RELATED APPLICATION

This application is a continuation-in-part of prior application Ser. No. 08/577,451, filed Dec. 22, 1995, now abandoned, and entitled Method for Modifying Catalyst Performance During the Gas Phase Synthesis of Vinyl Acetate.

BACKGROUND OF THE INVENTION

Field of the Invention

The present invention relates generally to the gas phase production of vinyl acetate. More specifically, the present invention is directed to a continuous or discontinuous series of modifications to the activity or selectivity of a catalyst during the gas phase production of vinyl acetate.

Definitions

Catalyst "performance" or "productivity" is intended to mean catalyst activity and/or selectivity. "Increased" catalyst performance or productivity is intended to mean increased catalyst activity and/or advantageously modified catalyst selectivity.

Discussion of the Prior Art

Vinyl acetate can be synthesized by the gas phase reaction of acetic acid with ethylene in the presence of oxygen. This gas phase reaction is typically conducted in the presence of a metal catalyst, typically palladium. The catalyst is typically placed upon a catalyst support. Co-catalysts can also be used, such as, gold, copper, barium or cadmium. The mount of public literature relating to this process is legion, and a more detailed discussion need not be given here. Literature relating to this process includes the following patents: U.S. Pat. No. 5,274,181; U.S. Pat. No. 5,347,046; U.S. Pat. No. 5,342,987; U.S. Pat. No. 5,336,802; U.S. Pat. No. 5,314,858; U.S. Pat. No. 5,332,710; U.S. Pat. No. 5,194,417; U.S. Pat. No. 5,179,056; U.S. Pat. No. 4,188,490; U.S. Pat. No. 4,370,492; U.S. Pat. No. 4,161,610; U.S. Pat. No. 3,567,767; U.S. Pat. No. 3,830,834; U.S. Pat. No. 3,658,888; U.S. Pat. No. 3,847,972; U.S. Pat. No. 3,634,496; U.S. Pat. No. 3,761,513; and U.S. Pat. No. 3,373,189.

In conventional processes, the catalyst is generally designed to provide maximum catalyst productivity within the design constraints of the particular process. In the gas phase synthesis of vinyl acetate, a common design constraint involves heat buildup within the catalyst during the reaction. Excessive heat can create safety hazards, can harm the catalyst, and/or can cause unwanted side-reactions. Another common design constraint relates to reagent concentrations, particularly oxygen concentration, due to explosion or fire concerns.

In a typical process, as the reaction is run at maximum catalyst productivity (within the design constraints of the particular process), the catalyst degrades. Although the reaction may be adjusted to some extent, generally speaking, the reaction slows as the catalyst degrades, and the process is ultimately shut down to replace the catalyst charge. Shut-downs are expensive, and a need therefore exists for increasing the productivity of a catalyst charge, while staying within the (safety and economic) parameters of the particular process.

SUMMARY OF THE INVENTION

Overview

The present invention is quite innovative, because a greater amount of catalyst can generally be used, relative to the above described conventional processes; as a result, the processes of the present invention generally need not be shut down as often for catalyst replacement. The additional amount of catalyst does not create a safety hazard (or other concerns) however; because rather than selecting a catalyst activator to run the system at maximum productivity, a "primary catalyst modifier" (a critical element of the present invention, which is further defined below) is used which is less effective in activating the catalyst than a "secondary catalyst modifier" (also a critical element of the present invention, which is further defined below).

The primary catalyst modifier is used, either alone or in combination with the secondary catalyst modifier, to initially activate the catalyst at a sufficiently low rate that the overall reaction stays below the safety limits (and other constraints) of the process. The secondary catalyst modifier is optionally used during this initial stage, where a balance between the two catalyst modifiers is used to control the productivity of the catalyst.

In one embodiment, the primary catalyst modifier is a catalyst deactivator or poison. The secondary catalyst modifier is used to increasingly offset (continuously or discontinuously) the deactivation effect of the primary catalyst modifier during the process.

As the process proceeds and the catalyst degrades, the secondary catalyst modifier is used (or increasingly used) to increase the productivity of the remaining (non-degraded) catalyst. The concentration of the secondary catalyst modifier need not always be increased—sometimes merely decreasing the concentration of the primary catalyst modifier in the feed stream or at the reaction site is sufficient to acquire the desired increase in catalyst productivity.

It has been surprisingly found that primary and secondary catalyst modifiers are sufficiently compatible to allow such fine tuning of the catalyst productivity. It has also been surprisingly discovered that the use of primary and secondary catalyst modifiers can increase the productivity of a catalyst charge, particularly where "excess" catalyst is incorporated into the catalyst charge (relative to conventional synthesis methods). In this way, the overall economics of the vinyl acetate synthesis process can be improved.

The Catalyst

The present invention is directed to a catalyst system for the gas phase synthesis of vinyl acetate, where ethylene is reacted with acetic acid in the presence of oxygen. The vinyl acetate reaction requires a catalyst, and the catalyst is preferably derived from palladium, although other conventional or non-conventional catalysts could be used, provided the catalyst degrades during the reaction process and provided the catalyst performance is affected by the primary and secondary catalyst modifiers as further described below. The catalyst can be in any form or any conventional or non-conventional catalyst format, provided the catalyst degrades over time during the vinyl acetate reaction process.

Primary Catalyst Modifier

The primary catalyst modifier is any composition which causes the catalyst to perform at a level below its maximum catalyst productivity. Preferred primary catalyst modifiers are oxo acids of boron, carbon, silicon, phosphorous, arsenic, antimony, sulfur or nitrogen, or a salt or acid salt derivative thereof. "Oxo acid" is intended to mean an organic or inorganic moiety comprising oxygen, wherein the oxygen is: 1. linked to another element by a double bond; or 2. linked to another element by a single bond and is also part of a hydroxyl moiety. For example, an oxo acid of phosphorous is phosphoric acid and an oxo acid of sulfur is sulfuric acid or sulfurous acid.

More preferred primary catalyst modifiers are oxo acids of sulfur, carbon, phosphorous, nitrogen or silicone, or a salt or acid salt derivative thereof. Yet more preferred primary catalyst modifiers are oxo acids of sulfur, carbon or phosphorous, or a salt or acid salt derivative thereof. Yet more preferred catalyst modifiers are acetates, sulfates, hydroxides, phosphates, pyrophosphates, and carbonates, and the most preferred primary catalyst modifier is monopotassium phosphate, monocesium phosphate, monorubidium phosphate, monopotassium pyrophosphate, monocesium pyrophosphate, monorubidium pyrophosphate, phosphoric acid or manganese acetate.

The primary catalyst modifier can be a catalyst activator or a catalyst deactivator. When the primary catalyst modifier is a deactivator or poison, then the secondary catalyst modifier is used to increasingly offset (continuously or discontinuously) such deactivation during the process. Likewise, when the primary catalyst modifier is an activator, the secondary catalyst modifier is used (alone or in combination with the primary catalyst modifier) to continuously or discontinuously increase the performance of the (non-degraded) catalyst.

Secondary Catalyst Modifier

The secondary catalyst modifier reduces greater catalyst productivity (with respect to the above described catalyst) than the primary catalyst modifier. The secondary catalyst modifier is typically also an oxo acid of boron, carbon, silicon, phosphorous, arsenic, antimony, aluminum, sulfur or nitrogen, or a salt or acid salt derivative thereof. Preferred secondary catalyst modifiers include potassium acetate, cesium acetate and rubidium acetate.

The catalyst activity induced by the secondary catalyst modifier divided by the catalyst activity induced by the primary catalyst modifier activity is greater than 1, preferably greater than 1.1, more preferably greater than 1.15, and yet more preferably greater than 1.25. A calculation of catalyst activity is provided in the examples of this specification; see particularly, the discussion section entitled "Examples 1-4 and Comparative Example 1" provided below. Ordinary skill and experimentation may be necessary in choosing a primary and secondary catalyst modifier for any particular process, or in choosing a primary catalyst modifier, once a secondary catalyst modifier is chosen.

Adjusting Catalyst Modifier Concentration

The primary catalyst modifier can be used in the feed stream and/or imbibed upon the catalyst (preferably added to the feed stream). A secondary catalyst modifier is also used and is preferably added to the feed stream. The primary and secondary catalyst modifiers need not be used at the same time, and one catalyst modifier can be used during a period in the process when the other is not used. Preferably, however, the two (or more) catalyst modifiers are used simultaneously in the process, during at least about 10%, yet more preferably at least 15% and yet more preferably at least 25% of the process cycle ("process cycle" is intended to mean the time from when the process is started up until the time the process is shut down for renewal or replacement of at least a portion of the catalyst). Either or both (or all of the) catalyst modifiers need not be present during the entire process, but one or the other should (and typically must) be present throughout substantially the entire process cycle.

During at least a portion of the process cycle in which catalyst degradation is occurring, the concentration of at least one of the catalyst modifiers will be adjusted, continuously or discontinuously. By altering the concentration of the primary catalyst modifier and/or altering the concentration of the secondary catalyst modifier, at least a portion of the remaining non-degraded catalyst is caused to continuously or discontinuously increase in catalyst activity or continuously or discontinuously (and advantageously) change in catalyst selectivity.

Preferably, the weight ratio of primary catalyst modifier to secondary catalyst modifier is continuously or discontinuously modified from an initial ratio of about 1:0-9 to a later ratio of 1:1-9. The "initial ratio" is hereby defined as occurring during the first quarter of the process cycle, and the "later ratio" is hereby defined as occurring during the fourth quarter of the process cycle. During the process cycle, preferably the weight ratio of primary catalyst modifier to secondary catalyst modifier is continuously or discontinuously decreased.

Preferably, the weight mount of primary catalyst modifier added (per unit time) to the feed stream (or imbibed upon the catalyst) is decreased by more than 25% during the process cycle; however, in some embodiments, the mount of primary catalyst modifier is not decreased or depleted, and the concentration of the secondary catalyst modifier is adjusted during the process. When the primary catalyst modifier is imbibed upon the catalyst, this change in primary catalyst modifier is preferably attributable to a washing away of the primary catalyst modifier from the catalyst by the reaction stream moving through the catalyst. Preferably, the weight amount per unit time of secondary catalyst modifier in the process is changed by at least about 10% during the life of the process.

The Final Process

In a preferred embodiment, the catalyst charge includes excess catalyst capacity. Such excess catalyst capacity is further defined as that amount of catalyst that would exceed the design limits of the particular process, if the process were initially run at or near maximum achievable catalyst activity, such as, by using an excess amount of secondary catalyst modifier and no primary catalyst modifier. An "excess" amount of secondary catalyst modifier is an amount which is so great that a further increase in amount of secondary catalyst modifier would have no significant additional effect upon the catalyst performance.

As the catalyst degrades, the secondary catalyst modifier is increasingly relied upon to increase catalytic productivity for the remaining non-degraded catalyst. In this way, the loss of (degraded) catalyst is wholly or partially offset by the increased performance of the remaining (non-degraded) catalyst.

This can be done by increasing the weight ratio of secondary catalyst modifier to primary catalyst modifier in the feed stream or at the reactive site as the process proceeds in time. It is theorized that the primary catalyst modifier impedes the secondary catalyst modifier, either by blocking active sites at the catalyst, by interacting with the secondary catalyst modifier so that the secondary catalyst modifier is less effective in activating the catalyst and/or by interacting with the active sites of the catalyst, making the secondary catalyst modifier less effective.

It is surprising that the relative amounts of primary and secondary catalyst modifiers can be adjusted to reliably adjust the performance of the catalyst, during the reaction process. An important feature of the present invention is that the activity of the catalyst is NOT maximized initially, but only increasingly adjusted toward maximum activity (with respect to non-degraded portions of the catalyst) as the catalyst degrades.

Naturally, more than one primary catalyst modifier and/or more than one secondary catalyst modifier can be used in alternative embodiments of the present invention. The number of primary or secondary catalyst modifiers is unimportant, provided at least one of each is used during the process and in accordance with the claims.

DETAILED DESCRIPTION OF THE PREFERRED EMBODIMENTS

TABLE 1

Figure 1:
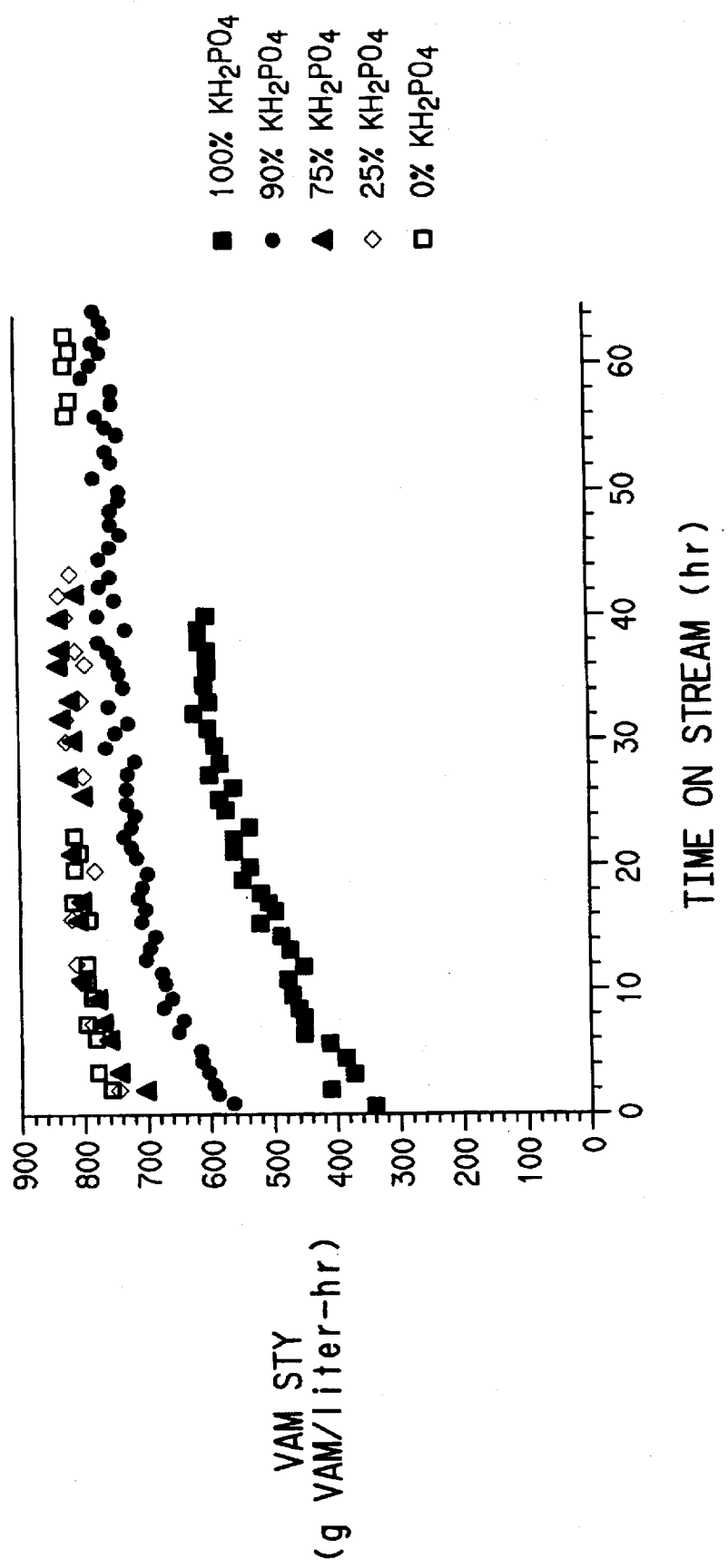
FIG. 1 is a graphical depiction of vinyl acetate space-time-yield (YAM STY) as a function of time on stream in fixed bed reactor for a 5.9 g/l Pd+2.6 g/l Au silica-supported catalyst for different ratios of $KH_2PO_4$ to KOAc with 0.31 moles/l cation and anion present. Each curve represents different ratios of $KH_2PO_4$ to KOAc, e.g., 75% $KH_2PO_4$+ 25% KOAc.

| Suitable Catalyst Modifiers | | |
|---|---|---|
| CsOAc | $H_3PO_4$ | $KHCO_3$ |
| KOAc | $KH_2PO_4$ | $K_2CO_3$ |
| NaOAc | $K_2HPO_4$ | $NaHCO_3$ |
| RbOAc | $K_3PO_4$ | $Na_2CO_3$ |
| $Mn(OAC)_2$ | $K_4P_2O_7$ | $CsHCO_3$ |
| $Ba(OAc)_2$ | $CsH_2PO_4$ | $Cs_2CO_3$ |
| $Cu(OAC)_2$ | $Cs2HPO_4$ | $RbHCO_3$ |
| $Mg(OAc)_2$ | $Cs_3PO_4$ | $Rb2CO_3$ |
| $Zn(OAc)_2$ | $Cs_4H_2PO_4$ | $K_2SO_4$ |
| $Pb(OAc)_2$ | $NaH_2PO_4$ | $KHSO_4$ |
| $Cd(OAc)_2$ | $Na_2HPO_4$ | $CsHSO_4$ |
| $Li(OAc)_2$ | $Na_3PO_4$ | $Cs_2SO_4$ |
| $Ca(OAc)_2$ | $Na_4H_2PO_4$ | $Na_2SO_4$ |
| NaOH | $RbH_2PO_4$ | $NaHSO_4$ |
| KOH | $Rb_2HPO_4$ | $Rb_2SO_4$ |
| RbOH | $Rb_3PO_4$ | $RbHSO_4$ |
| CsOH | $Rb_4P_2O_7$ | |
| $Na_2H_2P_2O_7$ | $NaH_3P_2O_7$ | |
| $K_2H_2P_2O_7$ | $KH_3P_2O_7$ | |
| $Cs_2H_2P_2O_7$ | $CsH_3P_2O_7$ | |
| $Rb_2H_2P_2O_7$ | $RbH_3P_2O_7$ | |

In a preferred embodiment of the present invention, an excess amount of catalyst is charged to the reactor, and the reaction initiated with a molar ratio of potassium acetate to monopotassium phosphate in the range of 0 to 0.11. As the active catalyst ages, the ratio in the feed stream is gradually increased to 0.33 or more, resulting in greater catalyst activity, thus compensating for the aging of the catalyst and maintaining high productivity without the usual penalties. It is to be understood that the specific applicable ratios will depend upon the primary and secondary catalyst modifiers chosen, and the specific reaction conditions.

Preferred for use as secondary catalyst modifier are the most effective catalyst activators found in Table 1. These include potassium acetate, cesium acetate, and rubidium acetate. Materials suitable for use as primary catalyst modifier are preferably drawn from the same compositions found suitable for use as secondary catalyst modifier, provided the catalyst productivity induced by the secondary catalyst is greater than the productivity induced by the primary catalyst. Most preferred for use as primary catalyst modifier are those which are among the less effective catalyst activators in Table 1. Preferred for use as primary catalyst modifiers are monopotassium phosphate, monocesium phosphate, monorubidium phosphate, monopotassium pyrophosphate, monocesium pyrophosphate, monorubidium pyrophosphate, phosphoric acid and manganese acetate.

Also suitable for use in the present invention are catalyst deactivators—species which retard the activity of the catalyst. Such species include sulfates, including $KHSO_4$, $K_2SO_4$, $NaHSO_4$, $Na_2SO_4$, $CsHSO_4$, $Cs_2SO_4$, $RbHSO_4$, $Rb_2SO_4$.

In a related embodiment of the present invention, it is found that an improvement in process control is achieved by continuously adjusting the molar ratio of secondary catalyst modifier to primary catalyst modifier in order to maintain precise control of reactivity and damp out unplanned excursions from the desired reaction conditions.

In the practice of this invention, it is preferable to adjust the molar ratio of secondary catalyst modifier to primary catalyst modifier by making fully or partly compensating adjustments in the feed rates of both ingredients in the process stream.

The catalyst preferred for the practice of this invention is preferably prepared in accordance with U.S. Pat. No. 4,048,096. It is found in the practice of the preferred embodiment of the present invention that it is advantageous to replace some or all of the potassium acetate imbibed into the catalyst according to the practice of the art with the monopotassium phosphate of the present invention.

In a preferred embodiment of the present invention the ethylene, acetic acid, oxygen, potassium acetate, and monopotassium phosphate are combined in a continuous gas feed stream to a catalyst bed made up of the preferred catalyst of the invention. On a mole-% basis, the composition of the feed stream is as follows: ethylene is present in the range of 40–90%, preferably 60–80%, acetic acid is present in the range of 5–40%, preferably 10–20%, oxygen is present in the range of 1–20%, preferably 5–10%, potassium acetate is present in the range of 0–1000 parts per million, preferably 0 to 100 parts per million, and monopotassium phosphate is present in the range of 0–1000 parts per million, preferably 0–100 parts per million. Amounts of potassium acetate or potassium phosphate above ca. 100 ppm should be employed only for short times because of the potential for excessive reactivation of the catalyst by either species.

In a preferred embodiment of the present invention, a 25–200%, preferably a 25–100%, excess amount of catalyst is charged to the reaction vessel. The catalyst so charged is preferably a catalyst made by the process in U.S. Pat. No. 4,048,096, wherein all the potassium acetate imbibed by the catalyst according to the practice of the art is replaced by monopotassium phosphate. The initial period of reaction, which depending on the specific configuration, may range from hours to months, is that period during which no adjustment to the acetate/phosphate ratio remains substantially unchanged. During the initial period of reaction, the ratio of potassium acetate to monopotassium phosphate in the feed gas stream would preferably be maintained between 0 and 0.1; and is in any event adjusted to provide the maximum permissible level of catalyst activity and selectivity.

The potassium acetate and monopotassium phosphate may be added to the feed stream or to the reaction vessel either batchwise or continuously.

When, by monitoring the vinyl acetate production rate, a decrease in catalyst productivity is detected, the feed rates of potassium acetate and potassium monophosphate are gradually adjusted in order to activate the catalyst in a controllable fashion, maintaining activity at or near the maximum permissible level, the adjustment in feed rate continuing until the catalyst has been fully activated.

In the preferred embodiment of the present invention the catalyst bed is maintained at a temperature in the range of 50° to 250° C., preferably 120° to 200° C., and at a process pressure of 0–300 psig (1–21.4 atmospheres), preferably 100 to 150 psig (7.8–11.2 atm). The gas hourly space velocity at standard temperature and pressure ranges from about 0–5000 $hr^{-1}$, preferably 500–4000 $hr^{-1}$.

It should be noted that the explosion limit under these process conditions generally lies in the range of about 5–15% of oxygen.

In the preferred embodiment of this invention, at a molar ratio of potassium acetate to monopotassium phosphate of 0.33 or greater, the catalyst productivity is the same as that achieved when no phosphate at all is present. In a particularly surprising aspect of the present invention, it has been found that the ratio of 0.33 represents an optimum and an improvement over the current art. Specifically, it has been found that at a ratio of 0.33 selectivity is at a maximum while productivity is also maximized. Thus in another embodiment of the present invention, an improvement in selectivity may be achieved. The optimum ratio of 0.33 is achieved with virgin catalyst. It is expected that the optimum ratio will change as the catalyst ages, but in any event the optimum will lie between ratios of 0.11 and 9. It will be obvious to one skilled in the art to determine the optimum ratio for a given set of conditions.

The attributes of the present invention are further indicated in the following specific embodiments.

EXAMPLES 1–4 AND COMPARATIVE EXAMPLE 1

In these examples, commercially available catalyst presumably prepared in accordance with U.S. Pat. No. 4,048,096 (or a derivation thereof) was obtained from Calsicat Division of Mallinckrodt Chemical, Inc., of Erie, Pa., USA. The catalyst consisted of 5 mm spherical silica beads impregnated with 5.9 g/l Pd, 2.6 g/l Au, and 40 g/l KOAc. In its as received condition, it was employed as the catalyst in Comparative Example 1.

A portion of the as-received catalyst was extracted with water in a soxhelet extractor at 100° C. for 72 hours to remove the water soluble KOAc from the catalyst. After extraction, it was then dried in air for 18 hours at 100° C. in a 1.8 ft³ (0.05 m³)—1.6 kW gravity oven at 100° C. in air for 18 hours in a Blue M oven, model SW-17TA-1 available from Blue M Electric Co., Blue Island, Fla. The extracted catalyst was then used in Examples 1–4 as follows.

Monopotassium phosphate ($KH_2PO_4$) and potassium acetate (KOAc) in the mounts shown in Table 2 were dissolved in 5.90 grams of water ($H_2O$) at room temperature. 10.0 grams of the dried, extracted catalyst beads hereinabove described are poured into the solution, rolled by hand until well coated, then let stand for a minimum of 1 hour. Over this 1 hour period occasional rolling of the catalyst takes place. The catalyst so treated was then dried in the Blue M oven hereinabove described, in air at 100° C. for at least 18 but not more than 60 hours.

TABLE 2

Amounts of KH2PO4 to KOAc used in catalyst series

| Example # | KOAc (g) | KH2PO4 (g) | H2O (g) | % KH2PO4 |
|---|---|---|---|---|
| 1 | 0.00 | 0.85 | 5.90 | 100 |
| 2 | 0.06 | 0.77 | 5.90 | 90 |
| 3 | 0.15 | 0.63 | 5.90 | 75 |
| 4 | 0.45 | 0.21 | 5.90 | 25 |

In each example, the reaction vessel was a cylindrical tube made from 316 stainless steel, with an outer diameter of 0.75 inches (1.9 cm), a wall thickness of 0.10 inches (0.26 cm) and a length of 15 inches (38.1 cm) which contained a thermowell threaded down the middle of the tube with an outer diameter of 0.0625 inches (0.159 cm). The tube was surrounded with a cylindrical aluminum casing 1.75 inch (4.44 cm) o.d./0.75 inch (1.9 cm) i.d. jacketed by a IH Co. (Stratford, Conn.) clamp heater model #B63489 rated at 750 kW and controlled by a Siemens 545 Program Logic Controller, available from Siemens Electronics, Johnson City, Tenn., via a model 7710 power pak available from Electrical Control Systems, Charlotte, N.C. The damp heater was 12 inches (30.5 cm) long by 1.5 inches (3.8 cm) inner diameter. 35 g (ca. 24 ml) of glass beads 90–106 µm in diameter, available as "Microbeads" from Cataphote, Inc., Jackson, Miss., were placed in the bottom of the tube, to a depth of ca. 6.5 inches (16.6 cm). 7.0 grams of catalyst (ca. 15 ml) was added, to an additional depth of ca 4 inches (10.2 cm). An additional Ca. 14 grams of microbeads were then used to fill the voids in the catalyst bed so prepared by manually tapping on the tube so filled. On top of the catalyst bed so prepared, an additional 24 g (ca. 17 ml) of microbeads were added to the reactor tube adding an additional 4.5 inches (11.5 cm) in depth.

The continuous gas phase synthesis of vinyl acetate was accomplished by flowing 390 sccm of ethylene ($C_2H_4$), 111 sccm (standard cubic centimeters per minute) of acetic acid (AcOH), 36 sccm of $O_2$, and 64 sccm of $N_2$ through the catalyst bed which were held at 115 psig (8.8 atm). The reactor wall and inlet gas stream were maintained at 150° C. The control thermocouple was placed in the thermal well about one inch (2.56 cm) above the catalyst bed.

Vinyl acetate space-time-yield (VAM STY) and selectivity (VAM SEL) were determined through conventional gas chromatographic techniques. Two Hewlett Packard (Model 5890 Series II) gas chromatographs were connected on-line at the reactor inlet and reactor outlet respectively. Nitrogen gas was used as an internal standard. The space-time yield (STY) of vinyl acetate is defined as the number of moles of vinyl acetate produced per hour per liter of catalyst. This can be determined by multiplying the catalyst's bulk density (grams of catalyst per reactor liter) by its specific activity (grams of vinyl acetate per hour per gram catalyst). VAM SEL is defined as the ratio of vinyl acetate produced per sum of vinyl acetate produced plus one-half the amount of carbon dioxide produced. Carbon dioxide is the major, and only detectable, by-product with the catalyst samples described herein.

The duration of the experiments was ca. 40–70 hours. For the purposes of the analysis, the catalyst behaved like virgin catalyst of stable composition throughout the test (except in Example 5 where the potassium acetate loading was purposely altered).

The STY data obtained is shown graphically in FIG. 1. In comparing the STY for 100% $KH_2PO_4$ with that for 100% KOAc (representative of the current art), it is clear that catalyst activity in the presence of $KH_2PO_4$ was more than 25% lower than in the presence of 100% KOAc, on an equimolar basis. The data also show that when the modification ratio was 1:3 or greater, catalyst productivity appeared to have been unaffected by the presence of the $KH_2PO_4$. That is, STY was relatively unaffected by $KH_2PO_4$ if the KOAc content was 25 mole % or greater.

Figure 2:
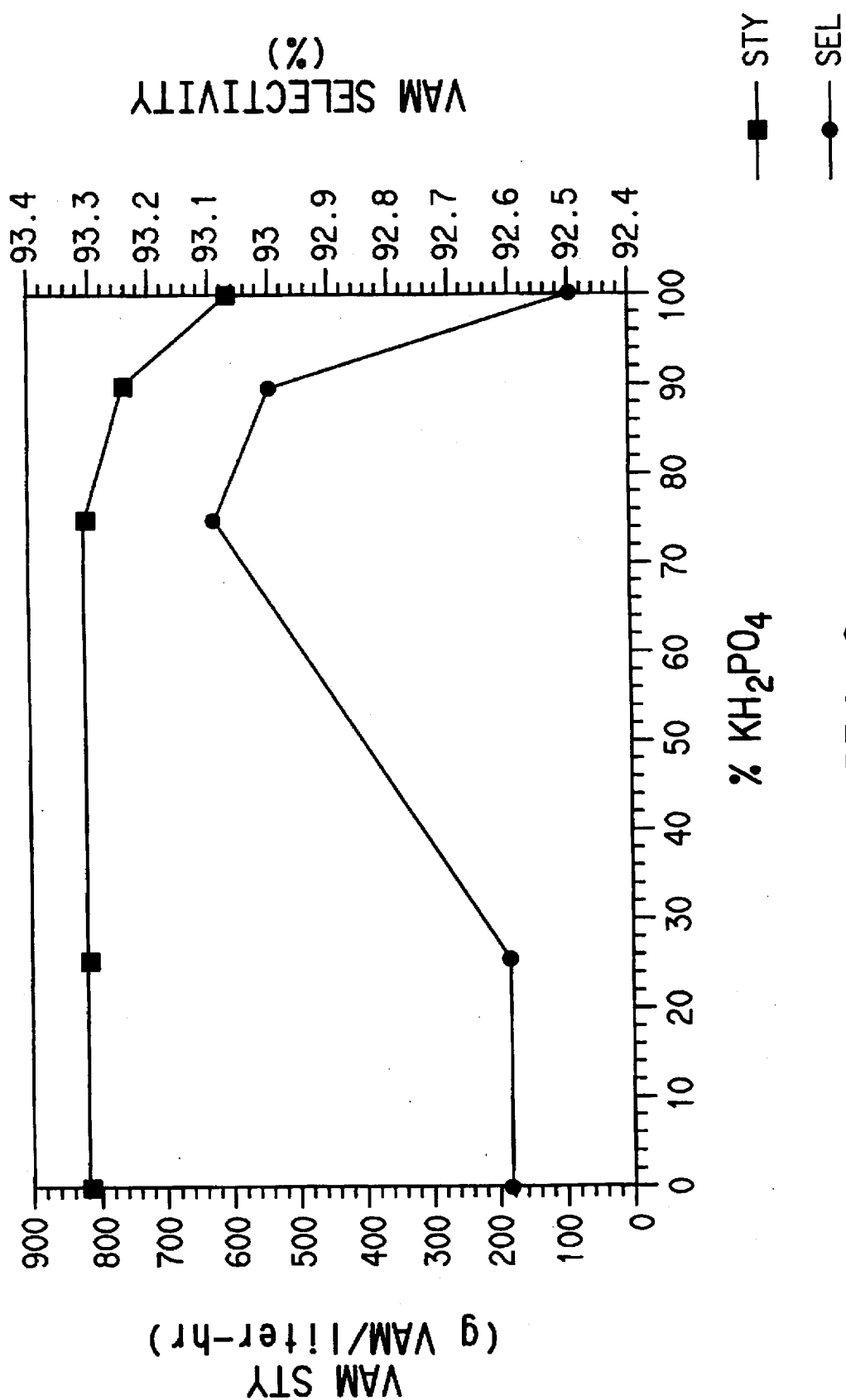
FIG. 2 is a graphical depiction of a summary of the role of $KH_2PO_4$ on the performance of a 5.9 g/l Pd+2.6 g/l Au silica-supported catalyst for different ratios of $KH_2PO_4$ to KOAc with 0.31 moles/l cation and anion present. Time on stream=40 hours, 150° C. reactor inlet, 115 psig total pressure, feed composition: 65% $C_2H_4$, 18% AcOH, 11% $N_2$, and 6% $O_2$ (mole %).

Selectivity data is shown graphically in FIG. 2. FIG. 2 represents steady state operating conditions at 40 hours into the run depicted in FIG. 1. At ca. 100 mole % $KH_2PO_4$ selectivity was lower than that at $KH_2PO_4$ concentrations below 25 mole %. However, in the range of 90 to less than 75 mole-% $KH_2PO_4$, selectivity was higher than that of Comparative Example 1.

EXAMPLE 5

A catalyst consisting of 5.9 g/l Pd, 2.6 g/l Au, and 51 g/l KH2PO4 was tested in the reactor facility using the configuration of Examples 1–4 except that there were no microbeads above the catalyst bed. After 75 hours of operation, 5 ml/hr. of a 0.19 wt % solution of potassium acetate in acetic acid was dripped onto the catalyst bed via a 1/16 inch (0.159 cm) o.d. and 0.020 inch (0.05 cm) i.d. 316 SS piece of tubing. This represented a concentration of 66 ppm of potassium acetate in the feed stream to the reactor. In order to maintain the acetic acid feed rate constant, the acetic acid feed stream was adjusted from 17 ml/hr. to 12 ml/hr. upon introduction of the potassium acetate/acetic acid solution.

Prior to the introduction of the potassium acetate co-feed stream, the catalyst was at a selectivity of ca. 93% and an STY of ca. 490. Forty hours after the introduction of the potassium acetate, the selectivity had increased to 95% ca. and the STY, to 770 ca.

EXAMPLES 6–13

In these examples, the catalyst was prepared by the method of U.S. Pat. No. 4,048,496, wherein the modifier imbibed into the catalyst support was as indicated in Table 3 hereinbelow. The reaction was run in the manner of Examples 1–4, and the space time yield (STY) and selectivity (SEL) were determined after the number of hours of reaction as indicated in Table 3. The molar concentration of cation was held constant at 0.33 moles/liter from example to example. The catalyst consisted of 5.9 g/l of palladium and 2.6 g/l of gold along with the modifier indicated.

TABLE 3

Selectivity and Space Time Yield – 0.33 moles/liter cation concentration

| Example | Modifier | SEL | STY | Hour |
|---|---|---|---|---|
| 6 | K4P2O7 | 93.9 | 780 | 42 |
| 7 | K3PO4 | 92.9 | 830 | 20 |
| 8 | K2HPO4 | 93.8 | 790 | 46 |
| 9 | KH2PO4 | 92.5 | 440 | 100 |

TABLE 3-continued

Selectivity and Space Time Yield – 0.33 moles/liter cation concentration

| Example | Modifier | SEL | STY | Hour |
|---|---|---|---|---|
| 10 | KOAc | 92.4 | 860 | 26 |
| 11 | KHSO4 | 37.5 | 20 | 36 |
| 12 | NaHSO4.H2O | 30 | 10 | 40 |
| 13 | NaH2PO4.H2O | 89.0 | 320 | 40 |

EXAMPLES 14–18

The reaction conditions in these examples were the same as in Examples 1–4 except that the control thermocouple was positioned within the thermal well to be in about the center of the catalyst bed instead of placed in the thermowell, and the temperature was 160° C. The catalyst consisted of 7.8 g/l of palladium, 3.4 of gold, and 35 g/l potassium acetate plus the amount of phosphoric acid indicated in Table 4. In these examples, STY and SEL were determined after 40 hours of reaction. An optimum in selectivity was achieved in the range of 20–29 g/l of phosphoric acid.

TABLE 4

Space Time Yield and Selectivity - 35 g/l KOAc

| Example | H3PO4 (g/l) | SEL | STY |
|---|---|---|---|
| 14 | 0 | 91.6 | 730 |
| 15 | 10 | 91.5 | 790 |
| 16 | 20 | 92.4 | 820 |
| 17 | 29 | 92.5 | 650 |
| 18 | 39 | 87.4 | 280 |

EXAMPLES 19–22

The reaction conditions for these examples were the same as in Examples 14–18 except that the catalyst consisted of 5.9 g/l of palladium, 2.6 g/l of gold, and a constant cation concentration of 0.32 moles/liter. The relative molar amounts of manganese and potassium being varied as indicated in Table 3. STY and SEL were determined after the number of hours of reaction time as indicated. Selectivity achieved an optimum at a Mn/K ratio of 70//30.

TABLE 5

Space time yield and Selectivity -- 0.32 m/l cation concentration

| Example | Mn(OAc)2 | KOAc | SEL | STY | Hour |
|---|---|---|---|---|---|
| 19 | 100% | 0% | 88.9 | 360 | 40 |
| 20 | 70% | 30% | 91.7 | 613 | 40 |
| 21 | 50% | 50% | 89.4 | 658 | 25 |
| 22 | 30% | 70% | 89.0 | 684 | 40 |

What is claimed is:

1. In a gas phase reaction of ethylene with acetic acid in the presence of oxygen and catalyzed by a charge of a metal catalyst, the metal catalyst being degraded over time due to the reaction, a method for improving the performance of the catalyst charge, the improvement comprising:

(a) adding an excess amount of catalyst to the catalyst charge so that the total amount of catalyst would exceed the design limits of the process, if the process were initially run at maximum achievable catalyst activity;

(b) adding a primary catalyst modifier to the feed stream or imbibing the primary catalyst modifier onto at least a portion of the catalyst or a catalyst support, wherein the primary catalyst modifier changes the productivity of the catalyst;

(c) adding a secondary catalyst modifier to the feed stream, the secondary catalyst modifier being different from the primary catalyst modifier, wherein the secondary catalyst modifier increases the productivity of the catalyst, and wherein the catalyst activity due to the secondary catalyst modifier divided by the catalyst activity due to the primary catalyst modifier is greater than 1;

(d) initially running the process at less than maximum achievable catalyst activity; and (e) continuously or discontinuously altering the relative amounts of the primary catalyst modifier and secondary catalyst modifier, so that as the catalyst degrades during the reaction process, at least a portion of the remaining non-degraded catalyst is caused to continuously or discontinuously increase in productivity.

2. A process in accordance with claim 1, wherein the primary catalyst modifier and the secondary catalyst modifier are members of the group consisting of:

oxo acids of boron, carbon, silicon, phosphorus, arsenic, antimony, sulfur or nitrogen, or a salt or acid salt derivative thereof, at least when initially added to the process.

3. A process in accordance with claim 2, wherein the primary catalyst modifier and the secondary catalyst modifier are members of the group consisting of:

oxo acids of carbon, silicon, phosphorus, sulfur or nitrogen, or a salt or acid salt derivative thereof, at least when initially added to the process.

4. A process in accordance with claim 3, wherein the primary catalyst modifier is an acetate, hydroxide, phosphate, pyrophosphate, carbonate or combination thereof.

5. A process in accordance with claim 4, wherein the primary catalyst modifier is monopotassium pyrophosphate, monocesium phosphate, monorubidium phosphate, monopotassium pyrophosphate, monocesium pyrophosphate, monorubidium pyrophosphate, phosphoric acid or a combination thereof, and the secondary catalyst modifier is potassium acetate, cesium acetate, rubidium acetate or a combination thereof.

6. A method in accordance with claim 1, wherein the primary catalyst modifier and the secondary catalyst modifier are both present in the feed stream at least 10% of the time between a process start-up and a process shut down, and the concentration of primary catalyst modifier in the process is decreased by at least 10% or the mount of secondary catalyst modifier in the process is increased by at least 10% during the time between process start-up and process shut down.

7. A method in accordance with claim 1 wherein more than one primary catalyst modifier or more than one secondary catalyst modifier is used in the process.

8. A method in accordance with claim 1 wherein the primary catalyst modifier comprises a catalyst deactivator.

9. In a gas phase reaction of ethylene with acetic acid in the presence of oxygen and catalyzed by a charge of a metal catalyst, the metal catalyst being degraded over time due to the reaction, a method for improving the efficacy of the catalyst charge, the improvement comprising:

(a) adding a primary catalyst modifier to the feed stream or imbibing the primary catalyst modifier onto at least a portion of the catalyst or a catalyst support, wherein the primary catalyst modifier increases the productivity of the catalyst;

(b) adding a secondary catalyst modifier to the feed stream, the secondary catalyst modifier being different from the primary catalyst modifier, wherein the secondary catalyst modifier increases the productivity of the catalyst, and wherein the catalyst activity due to the secondary catalyst modifier divided by the catalyst activity due to the primary catalyst modifier is greater than 1; and (c) continuously or discontinuously altering the relative amounts of the primary catalyst modifier and secondary catalyst modifier, so that as the catalyst degrades during the reaction process, at least a portion of the remaining non-degraded catalyst is caused to continuously or discontinuously increase in productivity, wherein the primary catalyst modifier and the secondary catalyst modifier are members of the group consisting of:

oxo acids of boron, carbon, silicon, phosphorus, arsenic, antimony, sulfur or nitrogen, or a salt or acid salt derivative thereof;

at least when primary catalyst modifier and the secondary catalyst modifier are initially added to the process.

10. A process in accordance with claim 9, wherein the primary catalyst modifier and the secondary catalyst modifier are members of the group consisting of:

oxo acids of boron, carbon, silicon, phosphorus, sulfur or nitrogen, or a salt or acid salt derivative thereof;

at least when initially added to the process.

11. A process in accordance with claim 10, wherein the primary catalyst modifier is an acetate, hydroxide, phosphate, pyrophosphate, carbonate or combination thereof.

12. A process in accordance with claim 11, wherein the primary catalyst modifier is monopotassium pyrophosphate, monocesium phosphate, monorubidium phosphate, monopotassium pyrophosphate, monocesium pyrophosphate, monorubidium pyrophosphate, phosphoric acid or a combination thereof; and the secondary catalyst modifier is potassium acetate, cesium acetate, rubidium acetate or a combination thereof.

13. A method in accordance with claim 12, wherein the primary catalyst modifier is an oxo acid of sulfur, carbon or phosphorous, or an acid derivative or acid salt derivative thereof.

14. A method in accordance with claim 12, wherein the primary catalyst modifier and the secondary catalyst modifier are both present in the feed stream at least 10% of the time between a process start-up and a process shut down, and the concentration of primary catalyst modifier in the process is decreased by at least 10% or the amount of secondary catalyst modifier in the process is increased by at least 10% during the time between the process start-up and the process shut down.

15. A process in accordance with claim 9, wherein the weight ratio of primary catalyst modifier to secondary catalyst modifier is continuously or discontinuously decreased during the process.

16. A process in accordance with claim 15 wherein the primary catalyst modifier is monopotassium phosphate.

17. A process in accordance with claim 15 wherein the primary catalyst modifier is selected from the group consisting of mono- and di-potassium sulfate, mono- and di-sodium sulfate, mono- and di-cesium sulfate, mono- and di-rubidium sulfate.

18. A process in accordance with claim 15 wherein the secondary catalyst modifier is selected from the group consisting of potassium acetate, cesium acetate, and rubidium acetate.

19. A process in accordance with claim 15 wherein the secondary catalyst modifier is potassium acetate.

20. A process in accordance with claim 15 wherein the catalyst at the start of the process contains 0.1 to 1.0 moles/liter of monopotassium phosphate or potassium acetate or a mixture thereof.

21. A process in accordance with claim 15, wherein the catalyst bed is maintained at a temperature of 100°–250° C., the reaction is carried out at a pressure of 0–300 psig, and the gas hourly space velocity of the gas stream at standard temperature and pressure is 1–5000 $hr^{-1}$.

* * * * *